US012648741B2

(12) United States Patent
Altmann et al.

(10) Patent No.: US 12,648,741 B2
(45) Date of Patent: Jun. 9, 2026

(54) SYSTEM AND METHOD OF SYNCHRONIZATION OF BIOPOTENTIAL SIGNALS

(71) Applicant: BIOSENSE WEBSTER (ISRAEL) LTD., Yokneam (IL)

(72) Inventors: Andres Claudio Altmann, Haifa (IL); Vadim Gliner, Haifa (IL); Assaf Govari, Haifa (IL); Alon Boumendil, Haifa (IL); Dayan Siton, Pardes-Hana Karkur (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 328 days.

(21) Appl. No.: 18/213,313

(22) Filed: Jun. 23, 2023

(65) Prior Publication Data

US 2024/0423555 A1     Dec. 26, 2024

(51) Int. Cl.
| | |
|---|---|
| *A61B 5/346* | (2021.01) |
| *A61B 5/00* | (2006.01) |
| *A61B 5/339* | (2021.01) |

(52) U.S. Cl.
CPC ............ *A61B 5/7285* (2013.01); *A61B 5/339* (2021.01); *A61B 5/346* (2021.01); *A61B 5/6852* (2013.01)

(58) Field of Classification Search
CPC ........ A61B 5/7285; A61B 5/346; A61B 5/339
USPC ......................................................... 600/509
See application file for complete search history.

(56) References Cited

U.S. PATENT DOCUMENTS

| | | | |
|---|---|---|---|
| 5,391,199 | A | 2/1995 | Ben Haim |
| 5,443,489 | A | 8/1995 | Ben Haim |
| 5,558,091 | A | 9/1996 | Acker |
| 6,172,499 | B1 | 1/2001 | Ashe |
| 6,239,724 | B1 | 5/2001 | Doron |
| 6,332,089 | B1 | 12/2001 | Acker |

(Continued)

FOREIGN PATENT DOCUMENTS

EP           0374854 A2 *   6/1990   .............. A61B 5/08

OTHER PUBLICATIONS

Extended European Search Report received for European Application No. 24183586.7, mailed on Mar. 26, 2025, 21 pages.

(Continued)

*Primary Examiner* — Nadia A Mahmood

(57) ABSTRACT

Disclosed herein are novel systems and methods for synchronized streaming of electrocardiogram (ECG) signals to a display. An aspect to the invention provides for synchronizing between first and second pluralities of digitized ECG signals that are sampled from a plurality of medical devices by first and second non-synchronized utilities. One of the pluralities of analog ECG signals, preferably a far-field ECG, is selected for reference and sampled by both the non-synchronized utilities thereby yielding respective first and second digitized reference ECG signals. The reference ECG signals are compared and the results of the comparison is used for synchronizing between the first and second pluralities of digitized ECG signals. Accordingly, the techniques of the invention facilitate concurrent synchronized streaming to a display, of a plurality of digitized ECG signals from a plurality of non-synchronized medical devices. Additional aspects and features of the invention are further disclosed herein.

22 Claims, 6 Drawing Sheets

(56)    References Cited

U.S. PATENT DOCUMENTS

| | | |
|---|---|---|
| 6,484,118 B1 | 11/2002 | Govari |
| 6,618,612 B1 | 9/2003 | Acker |
| 6,690,963 B2 | 2/2004 | Ben Haim |
| 6,788,967 B2 | 9/2004 | Ben Haim |
| 6,892,091 B1 | 5/2005 | Ben Haim |
| 7,536,218 B2 | 5/2009 | Govari |
| 7,756,576 B2 | 7/2010 | Levin |
| 7,848,787 B2 | 12/2010 | Osadchy |
| 7,869,865 B2 | 1/2011 | Govari |
| 8,456,182 B2 | 6/2013 | Bar-Tal |
| 2009/0131762 A1 | 5/2009 | Pelzek et al. |
| 2013/0023746 A1 | 1/2013 | Kilim |
| 2014/0169162 A1 | 6/2014 | Romano et al. |
| 2016/0296124 A1 | 10/2016 | Wegerich |
| 2020/0138302 A1 | 5/2020 | Edwards et al. |
| 2021/0044533 A1 | 2/2021 | Drakulic et al. |
| 2021/0186604 A1 | 6/2021 | Altmann |
| 2023/0052985 A1 | 2/2023 | Altmann |

OTHER PUBLICATIONS

European Search Report for corresponding EPA No. 24183586.7 dated Nov. 19, 2024.

* cited by examiner

180 - A method to synchronize streaming of ECG signals for display

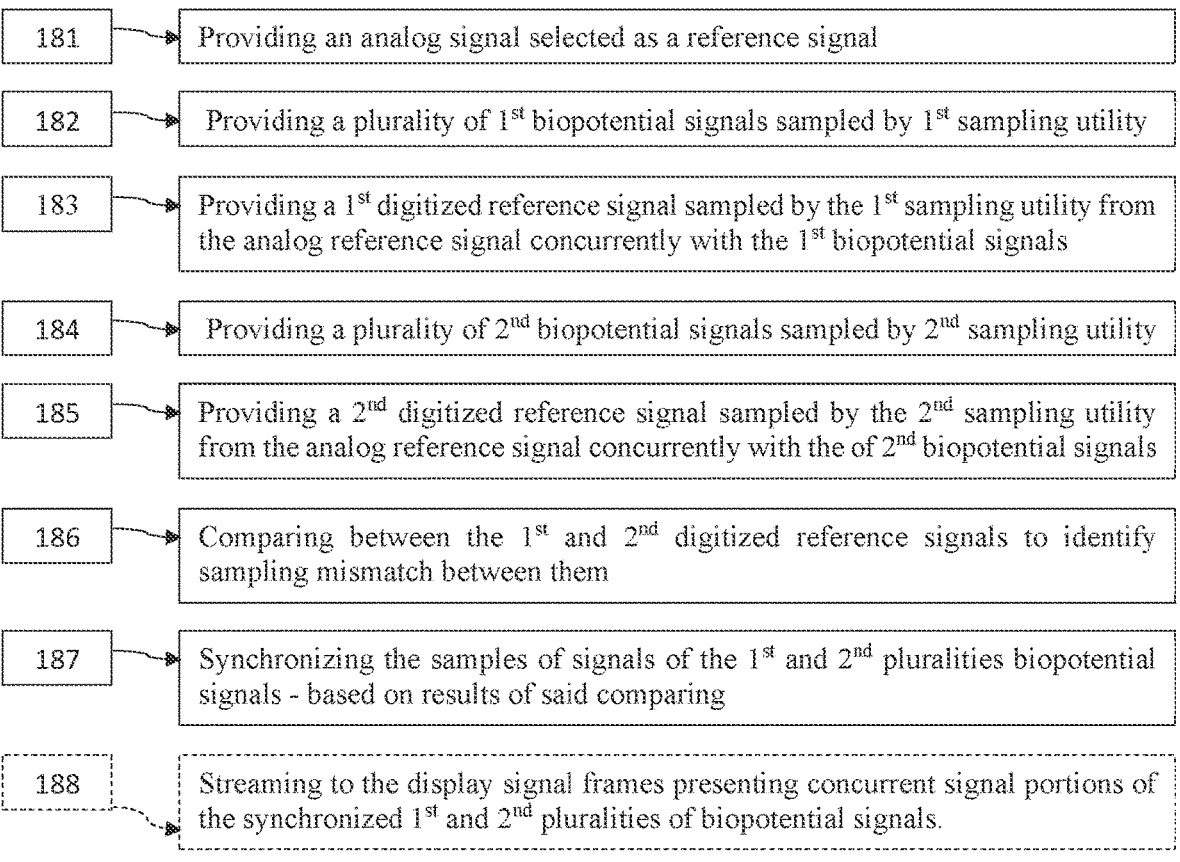

181 → Providing an analog signal selected as a reference signal

182 → Providing a plurality of 1st biopotential signals sampled by 1st sampling utility 183 → Providing a 1st digitized reference signal sampled by the 1st sampling utility from the analog reference signal concurrently with the 1st biopotential signals 184 → Providing a plurality of 2nd biopotential signals sampled by 2nd sampling utility 185 → Providing a 2nd digitized reference signal sampled by the 2nd sampling utility from the analog reference signal concurrently with the of 2nd biopotential signals 186 → Comparing between the 1st and 2nd digitized reference signals to identify sampling mismatch between them 187 → Synchronizing the samples of signals of the 1st and 2nd pluralities biopotential signals - based on results of said comparing 188 → Streaming to the display signal frames presenting concurrent signal portions of the synchronized 1st and 2nd pluralities of biopotential signals.

FIG. 3B

190 - A method to synchronize streaming of ECG signals for display

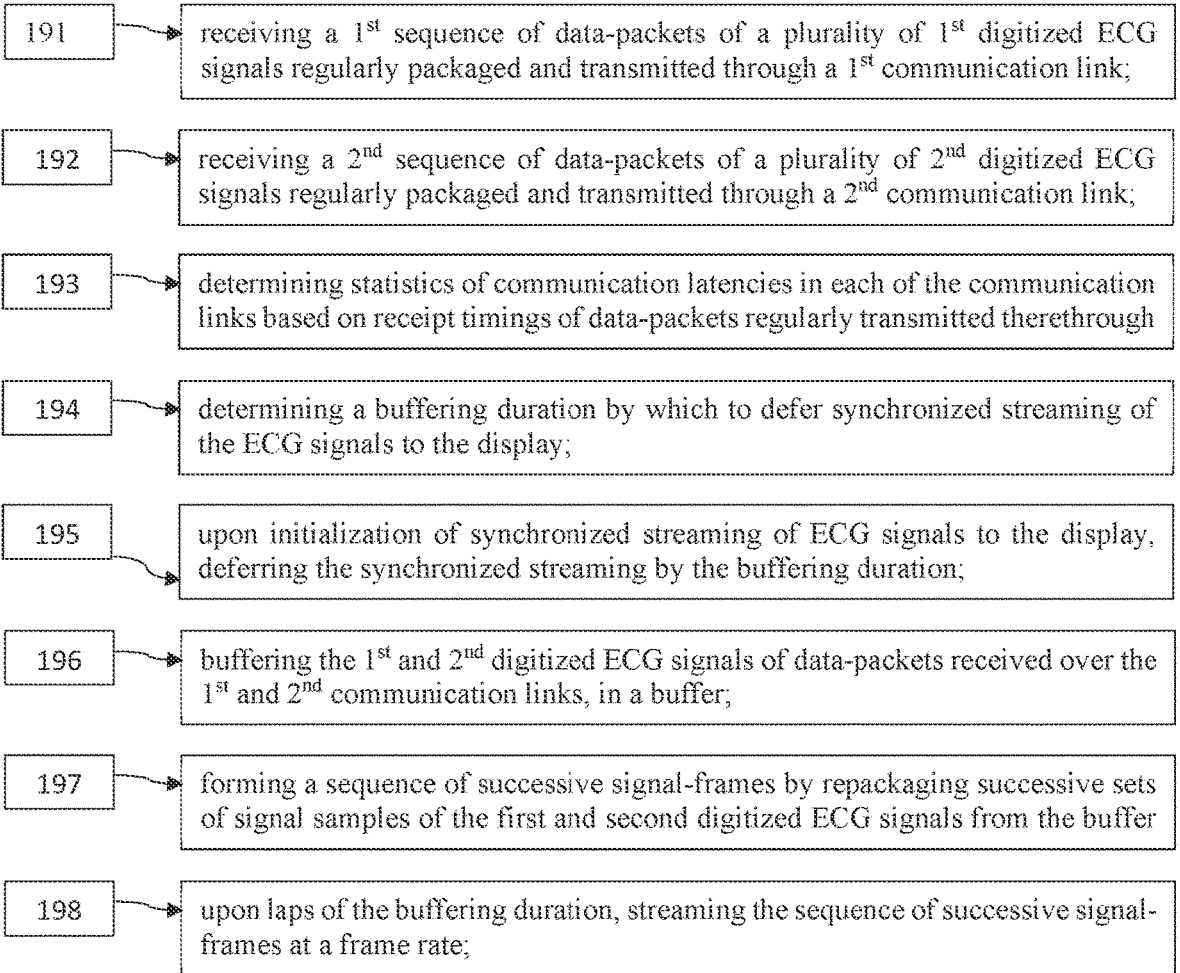

191 → receiving a 1st sequence of data-packets of a plurality of 1st digitized ECG signals regularly packaged and transmitted through a 1st communication link;

192 → receiving a 2nd sequence of data-packets of a plurality of 2nd digitized ECG signals regularly packaged and transmitted through a 2nd communication link;

193 → determining statistics of communication latencies in each of the communication links based on receipt timings of data-packets regularly transmitted therethrough 194 → determining a buffering duration by which to defer synchronized streaming of the ECG signals to the display;

195 → upon initialization of synchronized streaming of ECG signals to the display, deferring the synchronized streaming by the buffering duration;

196 → buffering the 1st and 2nd digitized ECG signals of data-packets received over the 1st and 2nd communication links, in a buffer;

197 → forming a sequence of successive signal-frames by repackaging successive sets of signal samples of the first and second digitized ECG signals from the buffer 198 → upon laps of the buffering duration, streaming the sequence of successive signal-frames at a frame rate;

FIG. 4B

SYSTEM AND METHOD OF SYNCHRONIZATION OF BIOPOTENTIAL SIGNALS

TECHNOLOGICAL FIELD

The present invention is in the field signal processing of physiological signals and particularly relates to synchronization of biopotential signals such as electrocardiogram (ECG) electrograms (EGM) and intracardiac-electrograms (IEGM) used in electrocardiogramonitoring during medical procedures.

BACKGROUND

A wide range of medical procedures involve placing probes, such as catheters, within a patient's body. One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Catheters are inserted into the heart chamber and optionally around the heart chamber during such procedures. In most procedures, multiple catheters are inserted into the patient. Catheters may include mapping, ablation, temperature sensing and image sensing catheters. Some catheters are dedicated for placement in specific parts of the anatomy, e.g., coronary sinus, esophagus, atrium, ventricle. The catheters have multiple electrical channels, some more than others depending on the number of sensors and electrodes included in each catheter. The number and type of catheters depends on the procedure and on the physician preferred workflow. During a procedure, the electrical activity of the heart is monitored from the catheter electrodes and sensors as well as from body surface electrodes attached to the patient's skin.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 3B is a flow diagram illustrating a method 180 for synchronizing between digitized ECG signals according to an embodiment of the present invention:

FIG. 4B is a flow diagram illustrating a method 190 for synchronizing between digitized ECG signals according to another embodiment of the present invention.

Figure 1:
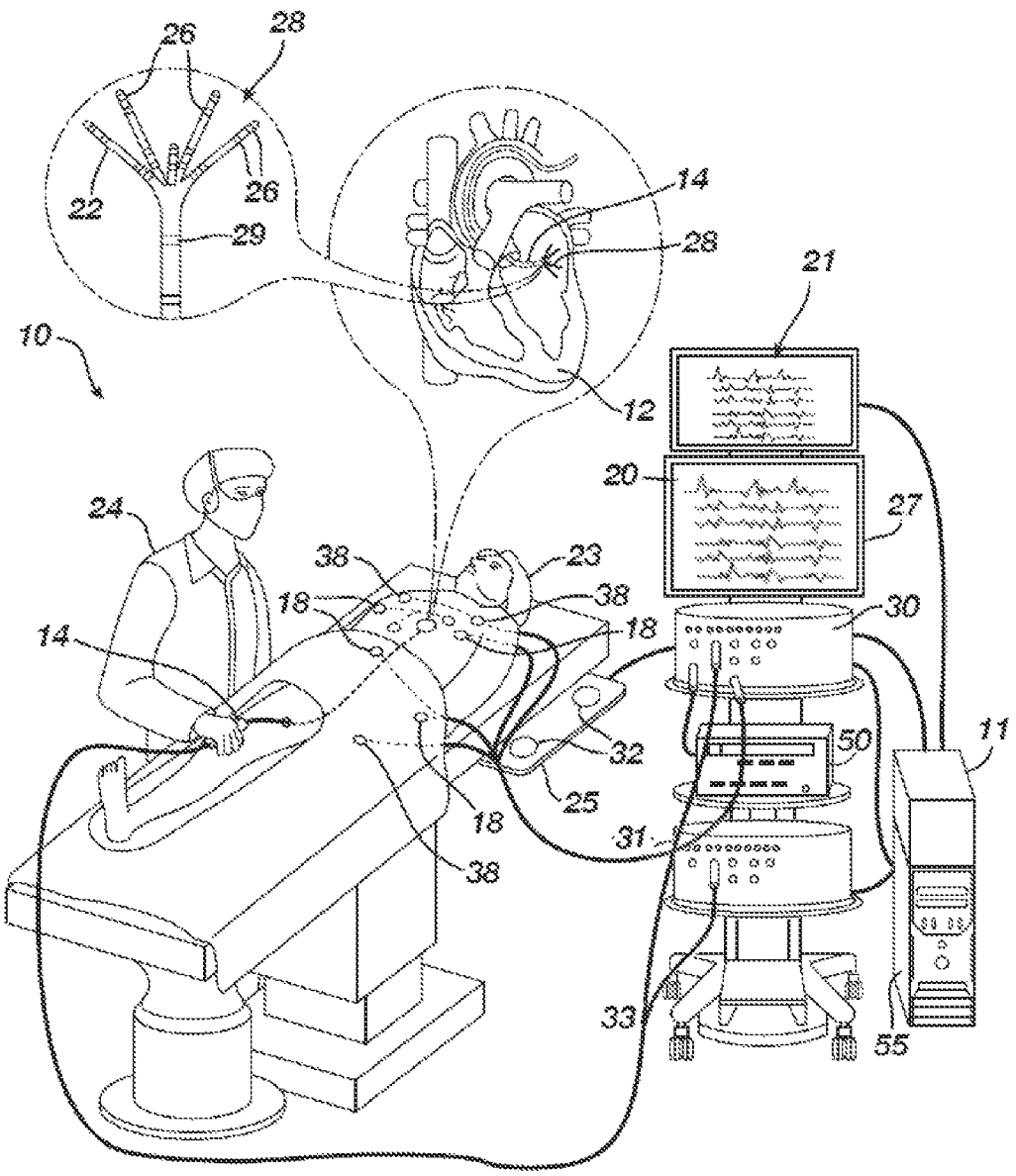
FIG. 1 is a schematic illustration showing a catheter-based electrophysiology mapping system 10 according to an embodiment of the present invention.

Like reference numerals are used in the figures of the present to designate similar modules/elements of the present invention or elements/modules having like functionalities. Accordingly, unless otherwise specified, description of modules/elements with reference to a certain embodiment of the invention should be understood to apply to all embodiments of the present invention in which such module/element is incorporated.

DETAILED DESCRIPTION OF EMBODIMENTS

Due to recent technological advancements, the number of sensors and electrodes that can be included in a catheter has increased significantly. For example, some diagnostic catheters include a distal end with 50 or more biopotential sensors (e.g., electrodes) for sensing electrical activity within a chamber of the heart. The large number of electrodes enables a physician to simultaneously capture the electrical activity from multiple locations in the heart chamber. A position sensor on the catheter records locations at which the electrical activity was sampled. The electrodes on the distal end include electrodes that are configured to engage with the tissue wall of the heart and sense near field biopotential signals and may also include a reference electrode configured to be immersed in the blood pool and sense far-field biopotential signal(s). The far-field signal may be used to remove any far field components that may be captured by the electrodes that are configured to engage with the tissue wall of the heart and sense near field signals.

There is a need in the art for novel systems and methods (e.g. medical devices) to enable collecting signals from the high density catheters. Conventional medical device already deployed in medical operation facilities typically have limited channels for collecting and simultaneously sampling sensory signals from high density (HD) catheters having for example 50 or more biopotential sensors (e.g. ECG electrodes), and cannot accommodate all the sensory channels of such HD catheters. During a medical procedure (diagnostic and/or therapeutic) there is a need to stream the output from all the sensors (ECG sensors) of multiple medical devices for display in a synchronized manner to the physician. However, the existing/deployed hardware which is generally adapted to collect, sample, and further communicated biopotential signals (ECG) from body surface electrodes as well as other catheters, is generally not suited for additionally collecting and sampling and communicating the additional sensory signals obtained from the high-density catheter(s). Mere addition of conventional hardware for collecting, sampling and/or communicating the signals from the HD catheters (e.g., separately from the already deployed hardware used for the signals of other electrophysiological equipment such as the body surface electrodes) does not facilitate synchronized sampling and/or communication of the signals from the HD catheters together with the signals from the other electrophysiological equipment. One reason for that being that such added hardware generally does not share the same sampling clock and the already deployed medical devices do not facilitated direct synchronization of its sampling clock with that of the added hardware. Another reason being that the added and the existing hardware communicate the signals obtained/sampled thereby (e.g., for streaming to the display) via separate communication data links which may introduced different latencies to the communication.

The present invention thus provides novel systems and methods for solving these problems to enable streaming of the biopotential signals obtained from HD catheters in synchronization with the biopotential signals obtained from other electrophysiological equipment such as the body surface electrodes and other catheters. Particularly, in certain aspects the invention facilitates achieving such synchronized streaming while without a need to replace the existing medical devices (e.g. which are already deployed), thus enabling to incorporate use of HD catheters in existing medical facilities in cost effective manner.

According to certain aspects of the present invention sample synchronization between the signals sampled by the existing and added hardware may be achieved by utilizing the output from one of the sensors of the HD catheter (which is herein after also referred to as reference analog signal) for synchronizing the between the sensory signals obtained from the HD catheter and the sensory signals obtained from the other electrophysiological equipment. The reference analog signal is split and provided for sampling by both existing and added hardware thereby yielding two digital reference signals presenting the sampling of the reference analog signal according to the sampling clocks of the respective existing and added hardware. Indeed, as these samplings may not be synchronized, extra sample(s) may be included in any one of the two digital reference signals for a given time period due to difference in sampling clocks by which they are sampled. However, since the two digital reference signals are sampled from a common reference analog signal, such extra sample(s) can be identified by comparison of the two digital reference signals. The identified extra sample(s) are then removed from the respective digital signals at which they exist thus synchronizing the samples of the digital signals sampled by the two sampling utilities and enabling their synchronized streaming to the display. The comparison between the digital reference signals may be performed often enough to identify and remove a single extra sample or only a few extra samples (e.g. up to 3) at each time, so as to maintain the continuous synchronization between the digital signals while avoiding apparent information gap in the displayed signals.

To facilitate the above procedure of sample's synchronization with an accurate and in-ambiguate identification of extra samples, signal which is selected for use as the reference analog signal for the synchronization should satisfy certain prerequisites as follows: it should be continuously non-stationary (e.g. continuously having non-constant value); and it should be non-periodic at least for the duration of each of the time intervals at which the comparison is performed to identify the extra sample(s) between the $1^{st}$ and $2^{nd}$ digital reference signals.

The present inventors have found that the far-field biopotential signal (e.g. far-field IEGM obtained from an HD catheter) satisfies these prerequisites for and is suitable for use as reference signal for the synchronization. This is because: 1. The far field biopotential signal is always present during the medical procedure, as opposed for example to near field signals that will only be captured based on touch or proximity of the electrodes to the tissue (e.g. skin/heartwall). 2. The far field biopotential signal is a biological signal and therefore not periodic. Accordingly in certain embodiments of the present invention the a far-field biopotential signal (e.g. obtained from a far-field IEGM sensor of an HD catheter) is specifically selected as the reference analog signal used for the synchronization process which is described above and in more detail below:

Reference is made to FIG. 1 showing an example catheter-based electrophysiology mapping and ablation system 10. System 10 includes multiple catheters, which are percutaneously inserted by a physician 24 through the patient's vascular system into a chamber or vascular structure of a heart 12. Typically, a delivery sheath catheter is inserted into the left or right atrium near a desired location in heart 12. Thereafter, one or more catheters may be inserted into the delivery sheath catheter so as to arrive at the desired location in heart 12. The plurality of catheters may include catheters dedicated for sensing Intracardiac Electrogram (IEGM) signals, catheters dedicated for ablating and/or catheters dedicated for both sensing and ablating. An example catheter 14, that is configured for sensing IEGM is illustrated herein. Physician 24 may place a distal tip 28 of catheter 14 in contact with the heart wall for sensing a target site in heart 12. For ablation, physician 24 may similarly place a distal end of an ablation catheter in contact with a target site for ablating tissue.

Catheter 14 is an exemplary catheter that includes one and preferably multiple electrodes 26 optionally distributed over a plurality of splines 22 at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,5391,199; 5,443,489:5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish location reference for location pad 25 as well as impedance-based tracking of electrodes 26. For impedance-based tracking, electrical current is directed to electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848, 787; 7,869,865; and 8,456,182.

A recorder 11 records and displays electrograms 21 captured with body surface electrocardiogram (ECG) electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between medical devices, such as catheters and/or other electrophysiological equipment, and a workstation 55 for controlling operation of system 10. The medical devices of system 10 include may include for example electrophysiological equipment such as one or more catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software stored therein, and user interface capability. Workstation 55 may provide multiple functions, optionally including (1) modeling the endocardial anatomy in three-dimensions (3D) and rendering the model or anatomical map for display on a display device 27, (2) displaying on display device 27 activation sequences 20 (or other data) compiled from recorded electrograms 21 in representative visual indicia or imagery superimposed on the rendered anatomical map, (3) displaying real-time location and orientation of multiple catheters within the heart chamber, and (4) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Figure 2:
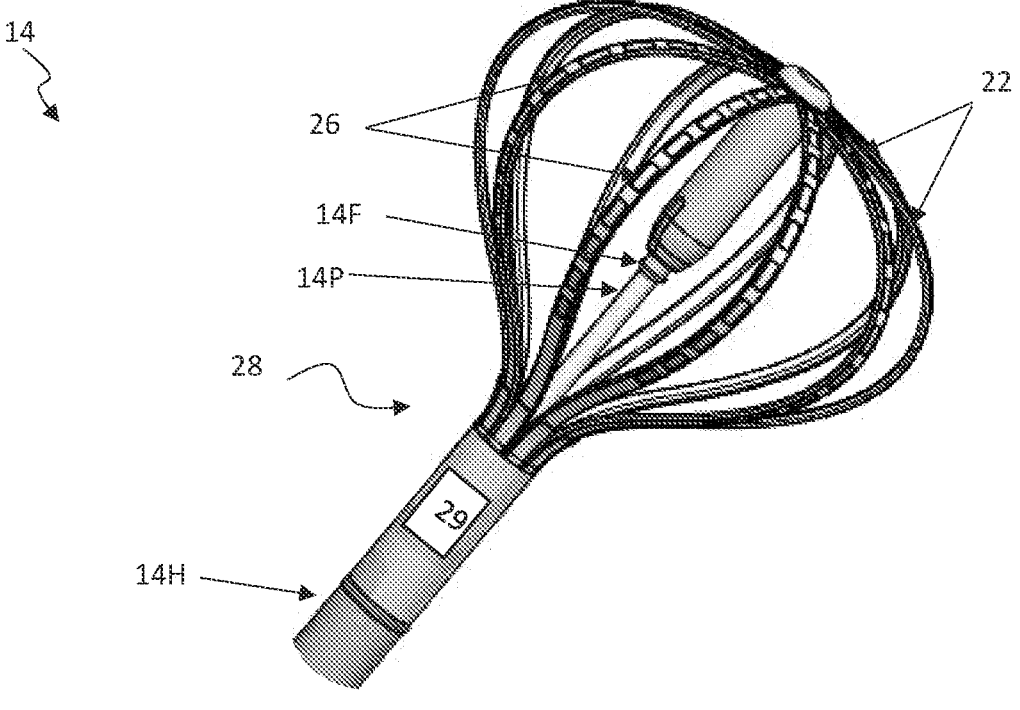
FIG. 2 is a schematic illustration of a catheter adapted to providing reference signal suitable for use with the synchronization systems and methods according to some embodiments of the present invention.

In the present example catheter 14 is a high density (HD) catheter 14 having for example 50 or more biopotential sensors (ECG electrodes). An example of such high-density catheter 14 is schematically illustrated in FIG. 2. The HD catheter 14 includes a shaft 14H with a position sensor 29 typically embedded in or near distal end 28 of the shaft 14H for tracking position and orientation of distal tip 28. The HD catheter 14 in this particular non-limiting example includes a pusher rode 14P passing through the shaft 14H and a plurality of splines 22 with multitudes of near-field intracardial electrogram sensors/electrodes 26 arranged thereon. The splines 22 are arranged near the distal end and form and expandable distal end assembly that can be deflectable outwardly from the catheter by moving the pusher rode 14P to thereby engage the near-field intracardial electrogram sensors/electrodes 26 in to contact with the tissue wall of the heart for sensing near-field signals IEGM signals (e.g. activation biopotential signals) when the catheter is located intracardially. The catheter 14 also includes a far-field intracardial electrogram sensor/electrode 14F (in this example arranged on the pusher rode 14P). The far-field IEGM sensor/electrode 14F is configured to be maintained spaced from the intracardial tissues during operation of the catheter, while being be immersed in the blood pool to measure/sense far-field biopotential signal (far-field IEGM). To this end the far-field IEGM sensor/electrode 14F is typically larger than the near-field electrodes 26 and configured with sufficient sensitivity for sensing the far-field IEGM signals. The far-field signal may be used for example in order to remove far field components that may be captured by the near-field electrodes 26.

It should be understood that the term biopotential signal/sensor is used herein to designate electrical physiological signals or sensors thereof, such as and not limited to electrocardiograms (ECG), electrograms (EGM) and intracardiac electrograms (IEGM).

It should also be noted that without loss of generality the terms electrocardiograms and ECG are used herein interchangeably to generally designate any type of biopotential signal. In this connection it should be noted that the term far-field with reference to biopotential signal is used herein to designate a biopotential signal, such as ECG, EGM and IEGM, that is measured by a suitable far-field sensor/electrode without contact with a body tissue of the patient (e.g. maintained spaced/separated from the tissue during measurement, while being possibly immersed in body fluid such as blood pool). Conversely the term near-field, is used herein with reference to biopotential signal to that are measured by sensors/electrodes designed to contact a body tissue of the patient (e.g. skin tissue or intracardiac tissue) for conducting the measurement.

Turning back to FIG. 1, as indicated above the electrophysiological equipment, such as the surface ECG device 38 which includes a plurality of ECG electrode patches attached externally to the patient's body/skin, as well as other electrophysiological equipment such as additional catheters (not specifically shown) are connected to the PIU which facilitate electrical communication between these electrophysiological equipment and the workstation 55. The PIU 30 may be for example adapted to apply analog to digital conversion (sampling) to the signals received from the electrophysiological equipment connected thereto, and/or pack these signals in data packets and communicate them to the workstation 55.

However, in some implementations of systems 10 (e.g., systems already deployed in medical operation facilities), the PIU 30 may have limited channels for collecting and simultaneously sampling/packing sensory signals and cannot accommodate the multitude of sensory channels provided by the multitude of electrodes 26 of an HD catheter 14 such as that exemplified in FIG. 2.

Therefore, in some implementation system 10 includes an additional signal processing unit (SPU) 31 which is configured and operable for complementing/extending the functionality of the PIU 30 to enable connection of additional medical devices, such as HD catheter 14, to the system 10. The SPU 31 is configured and operable to have one or more functionalities similar to those of the PIU 30 described above (not necessarily all the PIS functionality), so as to complement the PIU 30 and supporting the connection of additional medical devices, to the system 10. For example, SPU 31 provide interface for collecting and sampling/packing the signals from the HD catheter 14 or other electrophysiological equipment, and possibly also for connecting such electrophysiological equipment to the ablation energy generator 50, and/or recorder 11. Additionally, the SPU 31 may optionally implement processing capability for implementing real-time computations of location of the catheter(s) connected thereto or for performing ECG calculations.

Figure 3A:
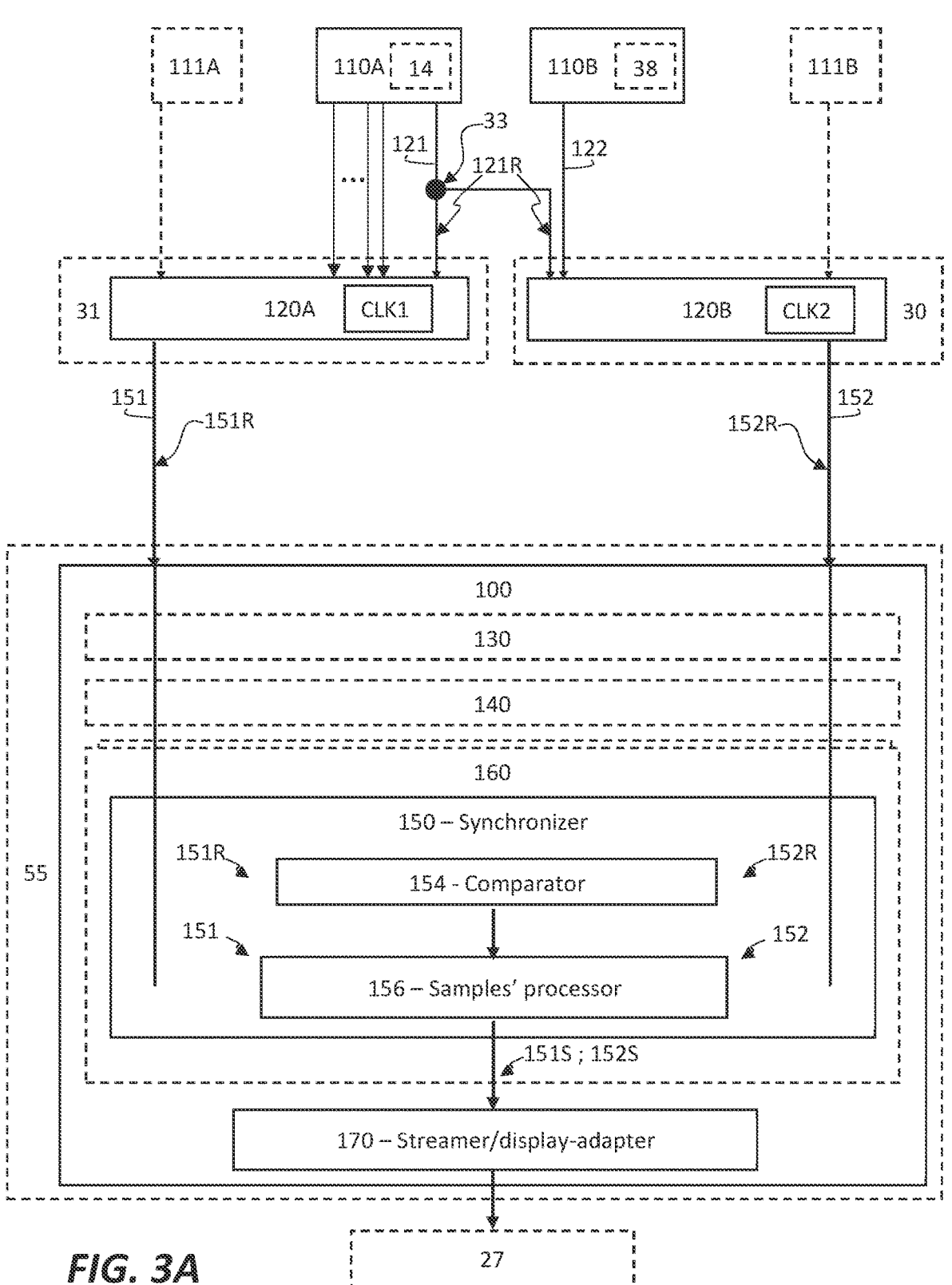
FIG. 3A is a block diagram illustrating the configuration of ECG signals synchronization system 100 according to an embodiment of the present invention.

Reference is now made to FIG. 3A which is a block diagram depicting the configuration of the synchronization subsystem 100 of the system 10 according to some embodiments of the present invention. In this embodiment, each of the SPU 31 and PIU includes a respective sampling utility, 120A and 120B. The sampling utilities, 120A and 120B, are respectively configured and operable for sampling analog biopotential signals sensed by the respective medical devices that are connected thereto, converting them to digitized biopotential signals 151 and 152, and further communicate them to the workstation 55. Workstation 55 in turn processes at least some of these biopotential signals 151 and 152 for display on display 27 (while optionally also utilizes these signals also to performs other processing such as ECG calculations, mapping, recording and the like).

As the sampling clocks CLK1 and CLK2 of the respective sampling utilities 120A and 120B of the SPU 31 and the PIU 30 are not inherently synchronized (e.g. the SPU 31 and PIU 30 may not include direct synchronization means for synchronizing their sampling clocks), the workstation thereof 55 is configured to synchronize the signals obtained therefrom and thereby compensate for this lack of synchronization.

To achieve that one selected sensory channel 121R of the HD catheter 14, is split by splitter 33 and directed for connection to both the SPU 31 (to which the rest of the sensory channels 121 of the HD catheter 14 are connected) as well as to an available port in the PIU 30 for sampling thereby as well. Splitter 33 may be any suitable signal splitter 33 such as for example a cable-integrated signal splitter or a signal switch. In this manner both SPU and PIU sample a common analog biopotential signal 121R (referend to herein as reference analog signal) that is obtained in this particular example from a sensory channel of the HD catheter 14 (e.g., from the far-field IEGM sensor thereof). The digitized reference signals 151R and 152R obtained from the sampling of that common analog biopotential signal 121R by the SPU 31 and PIU 30 respectively, are then provided to the synchronization system 100 of the workstation 55 and used to identify and compensate for a lack of synchronization between sampling utilities of the SPU 31 and PIU 30, as described below.

To this end, the synchronization system 100 is configured and operable to synchronize between digital biopotential signals 151 and 152 that are sampled by two or more non-synchronized sampling utilities 120A and 120B from a plurality of analog biopotential signals sensed by biopotential sensors (such as ECG and/or IEGM electrodes) of a plurality of medical devices connected thereto e.g., 110A and 110B 111A, 111B. More specifically, in this embodiment the system 100 includes a synchronizer 150 that is adapted synchronize the samples of the first and second pluralities of digitized signals, 151 and 152, that are respectively sampled by first and second non-synchronized sampling utilities 120A and 120B. In order to achieve that, synchronizer 150 receives the first plurality of digitized signals 151 which are obtained by the first sampling utility 120A, and which include the first digitized reference signal 151R obtained from sampling of the reference analog signal 121R by the first sampling utility, and also receives the second plurality of digitized signals 152 which are obtained by the second sampling utility 120B and which include the second digitized reference signal 152R obtained from the sampling of the reference analog signal 121R by the second sampling utility.

The synchronizer 150 includes a comparator 154 that is adapted to compare between the first and second digitized reference signals 151R and 152R, to identify discrepancy between their samples due to difference in the sampling rates between the $1^{st}$ and $2^{nd}$ sampling utilities 120A and 120B (this is based on the fact that the first and second reference signal are sampled from copies of the same underlaying analog reference signal 121R). Particularly, comparator 154 is adapted to identify when a shift between the two digitized reference signals is equal or larger than a one full digitized sample, in which case there is one (or optionally few samples, e.g., 3) extra sample that should be removed in order to synchronize the signals from the $1^{st}$ and 2nd sampling utilities 120A and 120B. It is noted that in case that a shift smaller than one sample is identified, there is no need to remove any extra samples and the signals from the $1^{st}$ and 2nd sampling utilities 120A and 120B may be considered synchronized until that time the shift grows to a duration of one sample or more. Additionally, the synchronizer 150 also includes a samples' processor 156 that is adapted to synchronize the samples in the plurality of the first digitized signals 151 with the samples of the plurality of the second digitized signals 152 based on the results/discrepancy identified by the comparator 154. More specifically, based on the extra sample(s) identified by the comparison, the samples processor 156 modifies the series of samples in each digitized signal of one of the first and second plurality of digitized signals which should be stream to the display, such that the series of samples in each such digitized signal corresponds to the series of samples of the signals of the other one of the first and second plurality of digitized signals for the same time frame. The samples processor 156 thereby provides synchronized signals 151S and 152S of the first and second pluralities of digitized signals 151 and 152 respectively.

Accordingly, the system 100 may include a streamer 170 (e.g. and/or a display adapter) that is configured and operable to concurrently stream/provide signal frames formed based on the synchronized biopotential signals 151S and 152S, for presentation of those biopotential signals 151S and 152S on the display 27.

It should be understood that in various implementations of the system 10, the biopotential/ECG signals synchronized by the system 100 are used not necessarily for display, or not only for the display, but for application of additional processing as may be required for the medical operation or for further analysis thereof or of medical condition of the patient. For instance, the biopotential/ECG signals synchronized by the system 100 may be stored for further analysis and/or used for computation activation sequences, representing indicia thereof in relation to anatomical maps, and/or displaying their relation to sites of interest such as places where ablation energy has been applied.

The operation of system 100 described above will now be described in more detail with reference to FIG. 3B in which a flow diagram illustrating a method 180 for synchronizing between digitized biopotential signals sampled by non-synchronized sampling utilities is presented according to embodiments of the present invention.

In 181, a selected analog reference signal 121R is provided for sampling by each of the non-synchronized sampling utilities 120A and 120B. Preferably, in various embodiments of the present invention a far-field biopotential signal (e.g. far-field ECG/IEGM) sensed by one of the medical devices, in the present example 110A, is selected/set to serve as the reference analog signal is 121R to be sampled by both/each sampling utilities.

Analog biopotential signals 121 from medical device 110A and possibly from additional medical device(s) such as 111A, are sampled by the first sampling utility 120A simultaneously with the sampling of the analog reference signal 121R. Accordingly the sampling by the first sampling utility 120B yields a first plurality of digitized signals 151 which are provided in 182. As shown in 183, the first plurality of digitized signals 151 thus provided, include a first reference digitized signal 151R which is obtained by the simultaneous sampling of the analog reference signal 121R by the first sampling utility 120A together with the sampling of signals 121.

In a similar manner, analog signals 122 from medical device 110B and possibly from additional medical device(s) such as 111B, are sampled by the second sampling utility 120B simultaneously with the sampling of the analog reference signal 121R by the second sampling utility 120B. Accordingly provided in 184 is a second plurality of digitized signals 152 sampled by the second sampling utility 120B. As shown in 185, the second plurality of digitized signals 152 includes a second reference digitized signal 152R which is obtained by the simultaneous sampling of the analog reference signal 121R by the second sampling utility 120B together with the sampling of signals 122.

Sampling clocks CLK1 and CLK2 of the respective sampling utilities 120A and 120B typically operate in practice at somewhat different frequencies, although they may have been designated for operating at a similar nominal sampling rate. This may be for example due to manufacturing variabilities or any number of environmental or power supply conditions affecting the operation frequency of the clocks (e.g. affecting frequency drifts). The frequencies of the sampling clocks are for instance in the order of 20 KHz and a difference between those frequencies may practically be substantially lower (for instance for a nominal frequency of 20,000 Hz, one of the clocks may operate and that nominal frequency and the other may drift by one or more Hz and operate for example at 19,999 Hz). It is noted that in general the frequency difference between the sampling utility 120A and 120B may not necessarily be constant or fixed and may in some embodiments vary due to various conditions (e.g., power-supply or temperature variations). Accordingly, the technique of the present invention for synchronizing the samples of those signals is also adapted for use in cases where the frequency different between the different sampling clocks is not constant.

Therefore, in view of said variations in the sampling frequencies, if one would to continuously display signals obtained from the different sampling utilities 120A and 120B under an assumption that their sampling clocks are in synchronization (e.g. based on the order samples obtained from these sampling utilities without being aware or accounting for their frequency difference), a shift between the displayed signals of the different sampling utilities would be accumulated over time.

Therefore, method operations 186 and 187 of method 180 are implemented respectively by the comparator 154 and the samples' processor 156, in order to synchronize the signal samples sampled by the two sampling utilities 120A and 120B, so as to prevent/mitigate the signal shifts described above and provide coherent and timely aligned presentation of the signals to the physician, In 186 the comparator 154 compares the first digitized reference signal 151R and the second digitized reference signal 152R (for example by cross correlation) in order to identify corresponding sections of samples between them. Accordingly, by the comparison performed in 186 extra sample(s) are identified in case one of the $1^{st}$ and $2^{nd}$ sampling utilities (e.g. 120B) operates at a higher sampling rate. In such case the comparison performed in 186 yields indication of extra sample(s) in a section of samples of the two digitized reference signal 152R that is sampled by the faster sampling utilities (e.g. 120B) as compared to a corresponding section of the digitized reference signal 151R sampled by the other sampling utility (e.g. 120A). In order to synchronize the signals from the first and second sampling utilities, the extra samples are removed in operation 187 from corresponding time frames of all of the signals which are to be displayed on display 27 and which are sampled by that sampling utility (e.g. 120B) that operates with the higher sampling rate.

To this end the operation 186 as well subsequent operation 187, may be performed iteratively for processing and synchronizing time frame portions of the signals of the $1^{st}$ and $2^{nd}$ sampling utilities that are to be displayed on the display 27. In this regard it should be understood that the successive iterations are be necessarily performed for comparing consecutive signal portions of the reference signals, and in general in some embodiments the iterations are performed at intervals that are sufficiently small to allow capturing of and removal of no more than a predetermined maximal number of extra samples threshold at each iteration (while preferably not being much more frequent than that so as not to overhead the processing system of the workstation 55 with unnecessary iterations).

In various embodiments of the present invention the predetermined threshold associated with the maximal number of extra samples to be identified in each iteration may be selected in the order of one or not more than few extra samples (e.g., a threshold of up to 3 extra samples to be identified in each iteration). Preferably the iterations are performed with time intervals that are sufficiently small to facilitate identification of only up to a single extra sample at each iteration (a threshold of 1). Operation with such small threshold (preferably one and not more then 3) may be important in order to prevent presentation of noticeable information gap in the signals displayed to the physician (a gap which might be formed in case larger number of extra samples is removed at-once/from-a-single-frame). Accordingly, a maximal time interval $\Delta T_{max}$ between successive iterations may be calculated based on the maximal number of extra samples threshold $\Delta S_{max}$ and the expected absolute maximal difference $\Delta F_{max}$ between the sampling rate $F_1$ at which the first sampling utility may operate and the sampling rate $F_2$ at which the second sampling utility may operate. For example, in some embodiments the maximal time interval may be set to $\Delta T_{max} = \Delta S_{max}/\Delta F_{max}$ such that if the maximal difference $\Delta F_{max}$ between the sampling rates is 10 Hz and the extra samples threshold $\Delta S_{max}$ is 1, the successive iterations are performed at least once for each 100 ms time frame of the signals. In practice in some embodiments the iterations may be performed at least once for every signal frame which is to be displayed on display 27, or more than that in case such required by the maximal time interval $\Delta T_{max}$ discussed above.

To this end, in operation 187 the samples' processor 156 operates to remove the extra samples which are sampled by the sampling utility operation at the faster sampling rate (e.g. 120B) from the corresponding sections of the signals that are obtained from that sampling utility. The removal of the extra samples is performed from the signals of the faster sampling utility, and which are to be presented on the display 27. In this regard, it should be understood that what is actually identified in operation 186 are sections/time-frames of the signals obtained from the faster operating sampling utility (e.g. 120B) at which there exist one or more extra samples(s) as compared to corresponding sections/time-frames in signal obtained from the other sampling utility (e.g. 120A). In general, the specific extra sample(s) to be removed from within each such section/time-frame may generally be arbitrary. Non-the-less, in some embodiment of the present invention, some criteria may optionally be applied to the selection the specific indices from which extra-samples removed from these section(s) in order to ensure no substantial information is lost from the display of the signals by removal of said extra-samples. One such criterion, which may be applied in some embodiments of the present invention, is that multiple extra samples to be removed will not be removed from consecutive sampling indices (e.g. that the removed extra samples will be distributed sparsely) so as not to form apparent gap/jump in the displayed signal by their removal. Another such criterion, which may be applied in some embodiments is that extra sample that is to be removed from a signal, will not be selected for removal from an extremum point of the signal (i.e., selected at sampling index that does not fall on extremal point) so that picks/valleys in the signal are properly displayed.

Thus, in operation 187, the samples' processor synchronizes 156 the signals of the first and second sampling utilities (at least those which are intended to be displayed), based on the results of the comparison made by the comparator 154 in operation 186, by removing extra samples identified by said comparison form the respective sections/time-frames of the signals at which the extra samples are identified. Accordingly, in operation 188, the synchronized signals obtained in operation 187 may be packed/compiled in display frames (e.g. showing the plurality of synchronized signals from both the sampling utilities in alignment with one another) and streamed for presentation on the display. The streaming may be performed at a frame rate of the display, whereby each displayed frame presents corresponding/aligned time section of the plurality of synchronized signals. Accordingly, the operations of method 180 may be performed iteratively, for preparing the set of synchronized signals for each displayed frame.

Moreover, it should be noted that typically in various embodiments of the present invention, the sampling resolution of the signals synchronized in operations 186 and 187 is set to be larger than display resolution in each time frame of the displayed frames (e.g. so that the number of samples/display-dots of the signals actually displayed on the display per each displayed time frame is smaller than the actual number of samples in the synchronized signals). Accordingly, in preparation of the display frames in operation 188, the synchronized biopotential signals 151S and 152S, which are obtained from operations 186 and 187, may be down-sampled to match the display resolution. This down sampling facilitates to avoid noticeable gaps appearing in the displayed frames due to the omission of the extra samples therefrom (since by the process of omission of sparse extra samples from a high-resolution signal, as obtained from 187, followed by down sampling of the signal to the lower display resolution, smooth-out/blurs any information gap if formed by such omission).

In this connection the inventors of the present invention have realized that a far-field biopotential signal (such as a far-field intracardial electrogram (far-field IEGM)) is particularly suitable for use as the reference analog signal 121 for the signal synchronization described above. In this regard, reliable and accurate implementation of the method 180 for synchronizing biopotential signals, particularly biopotential signals obtained during medical procedure, require proper selection of a suitable biopotential analog signal to be used as the reference signal 121 for the synchronization. Biopotential analog signal suitable for serving as the reference signal 121 for the purpose of the signal synchronization described above should be consistently non-stationary (e.g., not flat signal) though out the medical procedure, as well as non-periodic at least within a time duration of each displayed signal frame (which is typically in the order of 50 ms for display of about 20 frames-per-second (FPS)) suitable to serve as the reference signal. The present inventors have found that a far-field intracardial electrogram (far-field IEGM) signal obtained for example by the far-field sensor of HD catheter 14 is suitable for serving as the reference signal 121. Indeed, the far-field biopotential signal generally fulfills the above perquisites for the synchronization since the sensor(s) 14F configured for its measurement is highly sensitive to allow it to measure the signal without contact with the tissue an as a result a non-stationary signal is obtained thereby through the operation regardless of contact with the tissue; and also because due to its relatively high sensitivity it picks up substantial noise which is incorporated in the far field signal thus making the far field signal essentially non-periodic (e.g. within at least the relevant time duration of each displayed signal frame). Accordingly, the issue of connecting of the HD catheter 14 in synchronized manner, even to an already deployed system 10 whose PIU does not support sampling from of signals from the high number of sensors of such HD catheter 14, is facilitated by the technique of the present invention and preferably by exploiting that the far-field IEGM signal obtained from such catheter.

Thus, in some embodiments of the present invention preferably the far-field biopotential signal (e.g., the far-field IEGM obtained from catheter 14) is used as the reference analog signal 121 for the synchronization described above. In this regard it would be appreciated that it might be in general also possible to utilize one of the nearfield signals described above as reference signal for the synchronization of the present invention. However this might provide less reliable/consistent results, as those signals are less noisy and thus might be periodic (e.g. in line with periodicity of the heart activity), and also because acquiring the near-field signal depends on the contact maintained between the sensor/electrode sensing it and the body/heart tissue, and thus in an event of detachment of the sensor/electrode from the tissue a flat/stationary signal might be obtained preventing the implementation of the synchronization described above.

Therefore, turning back to operation 181 of method 180 in some embodiments of the present invention the analog reference signal 121R that is used for the synchronization and provided for sampling by each of the non-synchronized sampling utilities 120A and 120B, is preferably a far-field biopotential signal such as the far-field IEGM obtained from catheter 14.

With reference to FIG. 3A, as illustrated the system 100 may optionally additionally include modules/utilities designated in the figured by reference numerals 130, 140 and 160. The configurations and operations of these optional modules/utilities will be described in more details with reference to FIGS. 4A and 4B below, in which examples of synchronization system 100 and method 190 according to some embodiments of the present invention are illustrated.

As indicated above, another discrepancy which may be introduced by the addition of hardware for collecting and communicating the signals from the HD catheters separately from existing hardware used for collecting and communicating signals of other electrophysiological equipment is that the added and the existing hardware generally communicate the signals obtained thereby via separate communication data links, which may introduce different latencies to the communication, and thus discrepancies/time-lags between the displayed signals of the added and existing hardware in case they were to be directly displayed together.

Figure 4A:
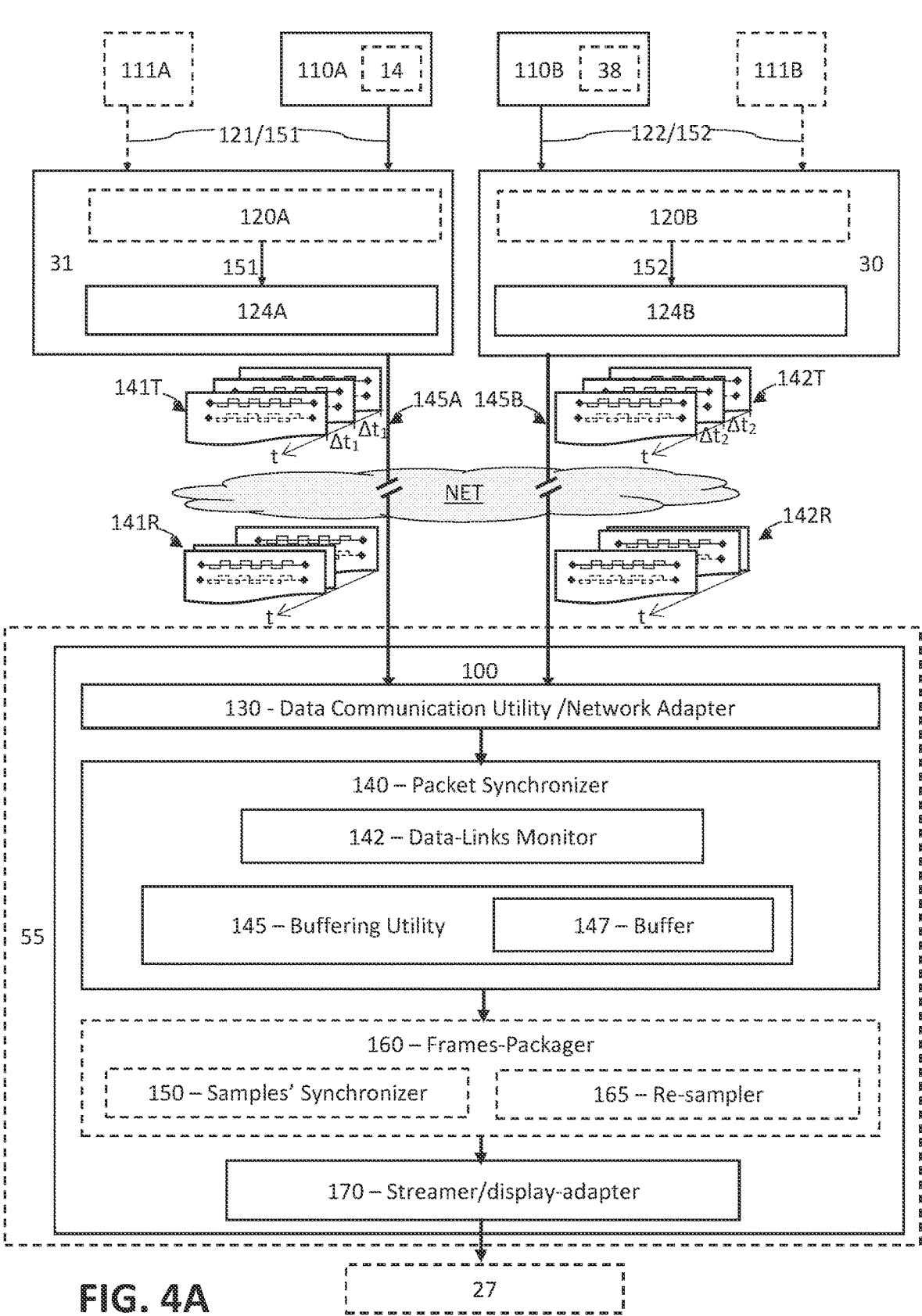
FIG. 4A is a block diagram illustrating a configuration of ECG signals synchronization system 100 according to another embodiment of the present invention.

Reference is now made together to FIGS. 4A and 4B illustrating the configuration and operation of the synchronization system 100 according to another embodiment of the present invention, which is adapted for applying communication/packet synchronization to synchronize between biopotential signals that are measured by different medical devices and collected and communicated to the system via different hardware. FIG. 4A is a block diagram depicting the configuration of the synchronization system 100 according to an embodiment of the present invention, and its connection with other modules/utilities of system 10. FIG. 4B is a flow diagram illustrating a method 190 for synchronizing between bio-signals sensed by sensors of several medical devices such as 110A and 110B of system 10 and acquired by respective the PIU 30 and SPU 31 utilities associated therewith.

The utilities 30 and 31 may be respectively connected to the medical devices 110A and 110B (and optionally to additional medical devices such as 111A and 111B) to receive analog biopotential signals, 121 and 122, or digital biopotential signals 151 and 152, sensed thereby. In cases where the biopotential signals are received in analog form, 121 and 122, the corresponding utility, i.e., utility 31 and/or 30, may include a respective sampling utility 120A or 120B adapted for sampling the respective signals to obtain the digitized form thereof 151 and 152. The SPU 31 and PIU 30 utilities also include respective network adapters 124A and 124B configured and operable for establishing respective communication data-links 145A and 145B between the respective utilities associated therewith and the workstation 55 through a data communication network NET, for communicating the respective digital biopotential signals 151 and 152 obtained thereby to the workstation 55.

The network NET may be for example any suitable data communication network such as LAN or WIFI or any other data communication network suitable implemented for communicating medical signals to the workstation 55 during medical procedures. The communication data-links 145A and 145B between the utilities 31 and 30 and the workstation 55 may be established for example based on TCP/IP protocol or like protocols providing reliable (e.g. validated) communication of data packets through the network. To this end network adapters 124A and 124B pack the respective bio-signals 151 and 152 obtained by their respective utilities 31 and 30, and send them in respective series of transmitted data packets, 141T and 142T, which are transmitted to workstation 55 through the corresponding data-links 145A and 145B established between the utilities 31 and 30 and the work station 55. The bio-signals 151 and 152 are typically sampled at constant rates and are therefore data packets of the series of transmitted data packets 141T and 142T are typically packed and transmitted by the utilities 31 and 30 at substantially regular time intervals $\Delta t_1$ and $\Delta t_2$ over time t as illustrated in FIG. 4A.

The synchronization system 100 in this embodiment is adapted to monitor the communication latencies with the different medical hardware (e.g., utilities 31 and 30) that collect the biopotential signals measured by the different medical devices, and accordingly adjusting the display timings of the signals so as to mitigate over these communication latencies, to enable their co-presentation in timely synchronized manner.

Synchronization system 100 includes a data communication utility 130 (e.g. network adapter) that is configured and operable to establish the first and second communication data-links 145A and 145B with the respective utilities 31 and 30 and to receive therethrough respective first and second received sequences of data-packets 141R and 142R in response to the sequences 141T and 142T transmitted by utilities 31 and 30. To this end the received first sequence of data-packets 141R includes a plurality of first digitized physiological/biopotential signals 151, which are sampled from sensors of at least one first medical device 110A and packed and transmitted over said first communication link 145A by the first utility 31; and the received second sequence of data-packets 142R includes a plurality of second digitized physiological/biopotential signals 152, which are sampled from sensors of at least one second medical device 110B and packed and transmitted over the second communication link 145B by the second utility 30.

As indicated above, the first and second sequence of data-packets 141R and 142R are preferably communicated utilizing reliable/validated communication protocol such as TCP in order to ensure their consistent receipt by the work station 55 so that signal portions packed by each data packet can consistently/reliably be displayed on display 27, without loss of signal information due to miscommunication of data packets.

However typically validated/reliable transmission protocols are less suited for real-time/pseudo-real-time operation and may introduce variable time-lags/latencies in the communication thereof. As a result of the variable latencies in the communication, time intervals between receipt of data packets in each of the first and second received sequence 141R and 142R and possibly the order of their receipt may vary with respect to the time intervals and order of their transmission 141T and 142T. Consequently, if the portions of the signals 151 and 152 provided by respective ones of these data packets were to be presented in the display 27 in actual full-real-time (i.e. as soon as the data packets are received), variable time lags between the presentation of different biopotential signal portions will be introduced in their presentation to the physician which might result with inconsistent and possibly misleading presentation of the biopotential signals to the physician.

The system 100 may therefore operate in pseudo-real-time with introduction of certain moderate time delay to the presentation not exceeding a certain time-delay threshold (e.g. of up to 150 ms) between the sensing of the biopotential signals and their presentation. Such pseudo-real-time operation facilitates consistent and timely ordered presentation of the biopotential signals 151 and 152 to the physician (mitigating the network latencies), while practically presentation of the biopotential signals to the physician with such moderate delays does not impair the medical procedure as the time lag introduced is on the one hand small enough so as not to be noticeable/meaningful for the medical operation, while on the other hand sufficient for establishing consistent presentation of the biopotential signals on the display 27.

To achieve that the system 100 includes a packet synchronizer 140 including a data-links monitor 142 and a buffering utility 145. The communication-links monitor 142 is connected to the data communication utility 130 and adapted to monitor receipt timings of data-packet of the data-packet sequences 141R and 142R received through each of the first and second data-links 145A and 145B. The communication-links monitor 142 thereby determines the statistics of latencies of communication of data packets through each of the first and second data-links 145A and 145B. The buffering utility 145 is configured and operable to utilize the statistic of the latencies of the data-links 145A and 145B to determine a buffering duration $\Delta T$ by which to defer streaming to the display 27, of the biopotential signals that are provided in data-packet of the data-packet sequences 141R and 142R. The buffering utility 145 is associated with a data-storage/buffer 147 (such as computer memory e.g., RAM) and is configured and operable for buffering in said buffer 147, portions of the first and second digitized biopotential signals 151 and 152 that are provided in the data-packet sequences 141R and 142R. The system 100 further includes a frame-packager 160 configured and operable to successively retrieve in data-packet of the data-packet sequences 141R and 142R from the buffer (e.g. after laps of the buffering duration) and repackage successive sets of samples of the portions of the biopotential signals 151 and 152 retrieved from the buffer 147, according to their sampling order, and utilize them to form a sequence of successive signal-frames which are to be streamed for display by display 27. Accordingly, the system 100 may include, or be associated with, a streamer 170 (e.g., which may for example be implemented by a display adapter or a network streamer) that is adapted to operate upon laps of the buffering duration for streaming said signal-frames to the display 27 at a predetermined/set frame rate.

As indicated above, in various implementations of the biopotential/ECG signals synchronized by the system 100 of this embodiment may be used not necessarily for display, or not only for the display, but optionally also carrying out additional processing. For instance, the biopotential/ECG signals synchronized by the system 100 may be stored for further analysis and/or used for computation of activation sequences, representing indicia thereof in relation to anatomical maps, and/or other processing as may be required.

The operation of system 100 will now be described more specifically with reference to the flow chart of method 190 illustrated in FIG. 4B.

Operations 191 and 192 which may be performed by the data communication utility 130 in parallel, the data communication utility 130 receives the $1^{st}$ and $2^{nd}$ sequences of data-packets in which generally $1^{st}$ and $2^{nd}$ digitized biopotential signals or portions thereof are received through the respective datalinks.

The statistics of the communication latencies in each of the datalinks 145A and 145B is determined in operation 193 by the data-links monitor 142. To this end the data-links monitor may be adapted to apply statistical processing to the receipt timings of data-packets from the respective $1^{st}$ and $2^{nd}$ utilities, 31 and 30, and thereby determine standard-deviations GA, OB, or variances of the latencies in transmission of data packets through each the data-links 145A and 145B respectively. It should be noted that in some embodiments the data-links monitor 142 may not obtain information about transmission times of the respective data packets and the statistical calculation may be performed under consideration of an operation scheme by which the data packets transmitted through each of the data-links 145A and 145B are transmitted in substantially regular/equal time intervals. Such operation scheme in which the data packets are practically transmitted through each data-link 145A or 145B at substantially regular/equal time intervals may be implemented in some embodiments of the present invention where the data packets carrying similar size portions (e.g. of similar durations/numbers-of samples) of the biopotential signals communicated thereby. Alternatively or additionally (e.g. in cases where the data packets may carrying biopotential signal portions of variable durations and not transmitted in fixed intervals), the data-links monitor 142 may utilize information of both the transmission times of the data-packets (which may be indicated in the respective data packets themselves) as well as their receipt timings by the network communication utility 130, in order to determine the latency statistics of the respective data-links 145A and 145B. It will be appreciated a person of ordinary skill in the art will readily appreciate how to determine the latency statistics of the data links in either the above techniques.

Thus, given the latency statistics, in operation 194 the buffering utility 145 determines a buffering duration ΔT by which to defer synchronized streaming to the display of the biopotential signals/portions thereof which are received through the data packets. Typically, the buffering duration ΔT is set to match a predetermined multiple n of a largest standard deviation among the standard deviations GA, OB in the latency statistics of the respective datalinks 145A and 145B, while not exceeding a predetermined maximal buffering threshold $\Delta T_{MAX}$ in order to facilitate pseudo-real-time presentation of the biopotential signals on the display 27. For example the buffering duration ΔT may be set as follows: $\Delta T = Min\ (n*Max\ (GA, OB), \Delta T_{MAX})$, whereby the predetermined multiple n may be set to within the range of 2.5 to 4 standard deviations (for example 3), and the maximal buffering threshold $\Delta T_{MAX}$ may be set to several tens of milliseconds, e.g. up to 150 ms or 200 ms. Accordingly deferring the streaming of the biopotential signals to the display 27 in this way yields a pseudo real-time presentation of the signals on the display while with vanishing likelihood of signal packets not being received in time for their display.

In operation 195, upon initialization of synchronized streaming of biopotential signals 151 and 152 to the display, the packet synchronizer 140 deferring the synchronized streaming by the buffering duration ΔT, and in operation 196 the buffering utility 145 operates to buffer/store the $1^{st}$ and $2^{nd}$ biopotential signals 151 and 152 received through the data-packets through the $1^{st}$ and $2^{nd}$ data-links, in the buffer 147.

In turn, in operation 197 the frame-packager 160 operates to generate a sequence of successive signal-frames presenting the portions of the biopotential signals 151 and 152 of which all counterparts were received through the data communication links 145A and 145B (e.g., stored in the buffer 147). This may include packaging and formatting successive sets of signal samples of the first and second pluralities of biopotential signals from the buffer according to their sampling order, to form a sequence of successive signal-frames to be displayed on the display 27. In this regard it should be understood that in some implementations overlapping sets of signal samples may be packaged in consecutive signal-frames so the display displays a video presenting a continuous/smooth change of the biopotential signals over time. It should be noted that in some embodiments the sampling resolution of the sets of signal samples of the biopotential signals is higher than the display/frame resolution of the signal frames presenting the biopotential signals on the display. In such embodiments the frame-packager 160 may include a re-sampler 165 configured and operable for resampling the sets of samples of the signals that are to be presented in the signal frames in order reduce their resolution and facilitate their presentation in sad signals frames.

Then, in operation 198 upon laps of the upon laps of the buffering duration (from the time of the initialization of synchronized streaming in operation 195), the sequence of successive signal-frames formed in operation 197 are streamed by the streamer/display-adapter 170 for display on the display 27.

System 100 and method 190 and of FIGS. 4A and 4B thereby provide packet synchronization for synchronizing between data-packets carrying bipotential signals of different medical devices communicated over different data-links of variable latencies and enable synchronized concurrent presentation of the bipotential signals sensed by the different medical devices in pseudo-real-time.

In some embodiments the system 100, e.g., the frame-packager 160 thereof, optionally also includes the synchronizer 150 that is described above with reference to FIGS. 3A to 3B. The synchronizer 150 may be for example operated according to the above-described method 180 for synchronizing between the samples of the sets of signal samples of biopotential signals that are packaged in each signal frame. More specifically the synchronizer processes the sets of signal samples to identify and remove extra samples obtained in one or more of the sets as a result of a difference between sampling rates of the first and second utilities, and thereby mitigates any mis-synchronization between sample sets sampled by non-synchronized sampling utilities of different medical devices. In such embodiments the system 100 applies both packet synchronization as well as sample synchronizations to the signals received from the plurality of medical devices.

It should be noted that the present invention was described above with specific reference to biopotential signals such as electrocardiograms (ECG), electrograms (EGM) and intracardiac electrograms (IEGN). In this regard as will be readily appreciated by those versed in the art, the methods and systems of the present invention are not limited to these specific biopotential signals and may be adapted for use with other biopotential signals and/or other physiological signals without departing from the scope of the invention.

EXAMPLES

Example 1. A method for synchronized streaming to a display of electrocardiogram (ECG) signals obtained from a plurality of medical devices, the method includes:

providing a plurality of first digitized signals including a first reference digitized signal whereby the plurality of first digitized signals are sampled by a first sampling utility from a plurality of first analog signals sensed by a plurality of first ECG sensors of a first medical device, and wherein one of said plurality of first analog signals is selected as a reference analog signal and said first reference digitized signal corresponds to a sampling of said reference analog signal by the first sampling utility;

providing a plurality of second digitized signals including a second reference digitized signal, whereby the plurality of second digitized signals comprise one or more second digitized signals sampled by a second sampling utility from one or more second analog signals sensed by one or more second ECG sensor of a second medical device in simultaneity with the sensing of the plurality of first analog signals, and said second reference digitized signal simultaneously sampled by the second sampling utility from the reference analog signal sensed by said first medical device;

comparing said first digitized reference signal to said second digitized reference signal;

synchronizing between said plurality of first digitized signals and said one or more second digitized signals based on said comparing; and concurrently streaming to the display said plurality of first digitized signals in synchronization with said one or more second digitized signals.

Example 2. The method according to example 1, including:

sensing said plurality of first analog signals by the plurality of first ECG sensors of the first medical device;

concurrently, sensing said one or more second analog signals by the one or more second ECG sensors of the second medical device;

sampling said plurality of first analog signals with said first sampling utility to obtain said plurality of first digitized signals including the first reference digitized signal; and sampling said one or more second analog signals and said reference analog signal with said second sampling utility to obtain said one or more second digitized signals and said second digitized reference signal:

Example 3. The method according to examples 1 or 2, wherein said synchronizing includes:

based on the comparing, identifying an extra sample obtained in each digitized signal of the first or second digitized signals that are obtained from one of the first or second sampling utility respectively, wherein the extra sample is results from a difference between sampling rates of the first and second sampling utilities; and removing said extra sample from each said digitized signal of the first or second digitized signals prior to said streaming to the display.

Example 4. The method according to any one of examples 1 to 3, wherein sampling clocks of said first and second sampling utilities operate with sampling rates in a vicinity of a similar nominal sampling rate.

Example 5. The method according to any one of examples 1 to 4, wherein each frame displaying by said ECG signals on the display presents a time interval of said ECG signals not exceeding a certain maximal duration, and wherein said reference analog signal is selected as one of said first analog signals being non-periodic and non-stationary within intervals of said certain maximal duration.

Example 6. The method according to example 5, wherein the reference analog signal is a far-field ECG signal.

Example 7. The method according to any one of examples 1 to 6, wherein said first and second medical devices comprise a plurality of ECG sensors that are adapted to sense said ECG signals in-situ during operation of the heart.

Example 8. The method according to example 7, wherein one or more of the following:

at least one medical device of said first and second medical devices is a catheter adapted for insertion in to a body for at least one of probing and treating a heart; and at least one of said first and second sampling utilities is connected to a plurality of ECG sensors of said catheter that are adapted to measure said cardiac activity in-situ, during operation of the heart;

at least one medical device of said first and second medical devices is a surface ECG device comprising a plurality of ECG sensors adapted for placement on a body, externally thereto, for probing a heart; and at least one of said first and second sampling utilities is connected to said plurality of ECG sensors.

Example 9. The method according to any one of examples 1 to 8, wherein the first medical device is a catheter adapted for being located within the heart during operation to sense intracardial electrogram (IEGM) signals and the reference analog signal is an ECG signal obtained from at least one ECG sensor of said catheter.

Example 10. The method according to any one of examples 1 to 9, wherein the catheter is adapted for insertion in to said heart and a plurality of ECG sensors of said catheter comprise multitude of ECG sensors arranged in the catheter for contacting a tissue of said heart during operation of the catheter, and at least one ECG sensor that is arranged in the catheter such that it is spaced from the tissue of the heart during the operation of the catheter, thereby enabling to sense a far-field ECG signal of the heart via said at least one ECG sensor and utilizing the far-field ECG signal as the reference analog signal.

Example 11. The method according to any one of examples 1 to 10, including applying further processing to the synchronized first and second digitized signals to analyze or compute one or more properties associated with said electrocardiograms.

Example 12. A method for synchronized streaming to a display of electrogram (ECG) signals obtained from a plurality of medical devices, the method includes:

receiving, via a first data-link associated with a first utility of a first medical device, a first sequence of data-packets comprising a plurality of first digitized ECG signals regularly packaged and transmitted over said first data-link by the first utility;

receiving, via a second data-link associated with a second utility of a second medical device, a second sequence of data-packets comprising one or more second digitized ECG signals regularly packaged and transmitted over said second data-link by the second utility;

monitoring the receipt timings of data-packets regularly transmitted over each of said first and second data-links to determine statistics of communication latencies in each of said data-links;

based on said statistics of the communication latencies determining a buffering duration by which to defer said synchronized streaming of the ECG signals to the display; and upon initialization of synchronized streaming of ECG signals to the display, deferring said synchronized streaming by said buffering duration;

buffering the first and second digitized ECG signals of the first and second sequences of data-packets received over said first and second data-links, in a buffer: # successively packaging successive sets of signal samples of said first and second digitized ECG signals retrieved from the buffer, according to their sampling order, to form a sequence of successive signal-frames to be streamed for display; and upon laps of said buffering duration, streaming said signal-frames to the display at a frame rate;

thereby mitigating said communication latencies and enabling pseudo real-time synchronized streaming to the display of ECG signals obtained via data-links associated with a plurality of medical devices.

Example 13. The method according to example 12, wherein said repackaging comprises carrying out the method of claim 1 for synchronizing between the signal samples of said first and second digitized ECG signals and identify and remove extra samples obtained in each digitized signal of the first or second digitized signals as a result of a difference between sampling rates of the first and second utilities.

Example 14. The method according to examples 12 or 13, wherein the repackaging includes down-sampling the signal samples of the first and second digitized ECG signals of said sets to from the signal frames with resolution suitable for presentation on the display.

Example 15. The method according to any one of examples 12 to 14, wherein the consecutive sets of the successive sets of signal samples, which are used to from said signal-frames, include overlapping signal samples.

Example 16. The method according to any one of examples 12 to 15, including determining standard deviations of the communication latencies of each the first and second data-links respectively and setting the buffering duration to match a predetermined multiple of a largest standard deviation of the standard deviations of the communication latencies.

Example 17. The method according to any one of examples 12 to 16, wherein the buffering duration is set to a multiple of at least three times the largest standard-deviation of the latency, while not exceeding a predetermined maximal buffering duration permitted for the streaming.

Example 18. A system to synchronize streaming to a display of electrocardiogram (ECG) signals obtained from a plurality of medical devices, the system includes:

a synchronizer adapted to receive first and second pluralities of digitized signals respectively sampled by first and second sampling utilities from a corresponding first and second pluralities of analog signals respectively sensed by ECG sensors of at least one first medical device and at least one second medical device;

wherein the first plurality of digitized signals includes a first reference digitized signal that is sampled by the first sampling utility from an analog signal of said first plurality of analog signals that selected as a reference analog signal and is sensed by an ECG sensor of the first medical device, which is selected as reference ECG sensor; and wherein the second plurality of digitized signals includes a second reference digitized signal that is sampled by the second sampling utility from said reference analog signal and is sensed by the reference ECG sensor of the first medical device;

the synchronizer includes:

a comparator adapted to compare between the first and second digitized reference signals; and a samples processor adapted for synchronizing between the plurality of first the digitized signals and the plurality of the second digitized signals based on results of comparison between said first and second reference signals performed by the comparator: thereby obtaining synchronized signals of the first and second pluralities of digitized signals; and the synchronizer being associated with a streamer that is adapted to concurrently stream to the synchronized signals of the first and second pluralities of digitized signals for display on the display.

Example 19. The system according to example 18, wherein the samples processor is configured and operable for synchronizing between the plurality of first the digitized signals and the plurality of the second digitized signals by:

identifying, based on the results of the comparison, an extra sample obtained in each digitized signal of one of the first or second plurality of digitized signals obtained from one of the first or second sampling utility respectively; and wherein said extra sample results from a difference between sampling rates of the first and second sampling utilities; and removing said extra sample from each said digitized signal of the first or second digitized signals.

Example 20. The system according to examples 18 or 19, wherein the first and second pluralities of digitized signals are ECG signals; and wherein each frame displaying the ECG signals on the display, presents a time interval of said ECG signals not exceeding a certain maximal duration; and said reference analog signal is selected as one of said first analog signals being non-periodic and non-stationary within intervals of the certain maximal duration.

Example 21. The system according to example 20, wherein the at least one first medical device includes a catheter that is adapted for being located within a heart during operation thereof to sense intracardiac electrogram (IEGM) signals; and wherein the reference ECG sensor is an ECG sensor arranged in the catheter such that it is spaced from a tissue of the heart during the operation and adapted to obtain the reference analog signal as a far-field ECG signal.

Example 22. The system according to any one of examples 18 to 21, wherein one or more of the following:

the system further includes at least one of the following:
the at least one first medical device: the at least one second medical device: the first sampling utility; the second sampling utility; and the display;

the at least one first and at least one second medical devices include a plurality of ECG sensors that are adapted to sense ECG signals in-situ during operation of a heart;

at least one medical device of the first and second medical devices is a catheter adapted for insertion into a body for at least one of probing and treating a heart; and at least one of the first and second sampling utilities is connected to a plurality of ECG sensors of the catheter;

at least one medical device of the first and second medical devices is a surface ECG device including a plurality of ECG sensors adapted for placement on a body, externally thereto, for probing a heart; and at least one of the first and second sampling utilities is connected to the plurality of ECG sensors.

Example 23. A system for synchronized streaming to a display of electrocardiogram (ECG) signals obtained from a plurality of medical devices, the system includes:

a data communication utility configured and operable to receive, via first and second communication links associated respectively with first and second utilities, respective first and second sequences of data-packets: whereby the first sequence of data-packets includes a plurality of first digitized ECG signals, which are sampled from ECG sensors of at least one first medical device and regularly packaged and transmitted over said first communication link by the first utility; and the second sequence of data-packets includes a plurality of second digitized ECG signals, which are sampled from ECG sensors of at least one second medical device and regularly packaged and transmitted over the second communication link by the second utility;

a packet synchronizer including:

a communication-links monitor that is connected to said data communication utility and adapted to monitor receipt timings of data-packets transmitted over each of the first and second communication links and thereby determine statistics of communication latencies of each of the first and second communication links; and a buffering utility including a buffer and configured and operable to utilize the statistics of the communication latencies to determine a buffering duration by which to buffer the first and second digitized ECG signals of the data-packets and defer streaming of the ECG signals to the display, in order to enable synchronized streaming of the first and second digitized ECG signals to the display; and wherein upon initialization of synchronized streaming of ECG signals to the display, the buffering utility is adapted to defer the synchronized streaming by the buffering duration, and buffer the first and second digitized ECG signals of the first and second sequences of data-packets received over the first and second communication links in the buffer: # a frame-packager configured and operable for successively retrieving and packaging successive sets of signal samples of said first and second digitized ECG signals stored in the buffer, according to their sampling order, to form a sequence of successive signal-frames to be streamed for display; and a streamer adapted to operate upon laps of the buffering duration for streaming the signal-frames to the display at a frame rate.

Example 24. The system according to example 23, wherein the communication-links monitor is adapted to process the receipt timings of the data-packets and thereby determine standard deviations of the communication latencies of each the first and second communication links respectively; and wherein the buffering utility is adapted to set the buffering duration to match a predetermined multiple of a largest standard deviation of the standard deviations of the communication latencies.

Example 25. The system according to example 23 or 24, wherein the frame-packager includes the synchronizer according to any one of examples 18 to 22, and is configured and operable for synchronizing between the signal samples of the first and second pluralities digitized signals and identify and remove extra samples obtained in each digitized signal of the first or second digitized signals as a result of a difference between sampling rates of the first and second utilities.

Example 26. The system according to any one of examples 23 to 25, wherein the frame-packager includes a re-sampler adapted to down-sample the first and second digitized ECG signals to from the signal frames with resolution suitable for presentation on the display.

It should be understood that the term electrocardiogram (ECG) is used in the above examples and in the present disclosure to designate in general any type of biopotential signal for which the systems and methods of the present invention may be applied.

It should also be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:

1. A method for synchronized streaming to a display of electrocardiogram (ECG) signals obtained from a plurality of medical devices, the method comprising:

providing a plurality of first digitized signals including a first reference digitized signal whereby the plurality of first digitized signals are sampled by a first sampling utility from a plurality of first analog signals sensed by a plurality of first ECG sensors of a first medical device, and wherein one of said plurality of first analog signals is selected as a reference analog signal and said first reference digitized signal corresponds to a sampling of said reference analog signal by the first sampling utility;

providing a plurality of second digitized signals including a second reference digitized signal, whereby the plurality of second digitized signals comprise one or more second digitized signals sampled by a second sampling utility from one or more second analog signals sensed by one or more second ECG sensor of a second medical device in simultaneity with the sensing of the plurality of first analog signals, and said second reference digitized signal simultaneously sampled by the second sampling utility from the reference analog signal sensed by said first medical device;

comparing said first digitized reference signal to said second digitized reference signal;

synchronizing between said plurality of first digitized signals and said one or more second digitized signals based on said comparing, wherein said synchronizing comprises;

based on the comparing, identifying an extra sample obtained in each digitized signal of the first or second digitized signals that are obtained from one of the first or second sampling utility respectively, wherein the extra sample results from a difference between sampling rates of the first and second sampling utilities, and removing said extra sample from each said digitized signal of the first or second digitized signals prior to said streaming to the display; and concurrently streaming to the display said plurality of first digitized signals in synchronization with said one or more second digitized signals.

2. The method of claim 1 comprising: sensing said plurality of first analog signals by the plurality of first ECG sensors of the first medical device; concurrently, sensing said one or more second analog signals by the one or more second ECG sensors of the second medical device; sampling said plurality of first analog signals with said first sampling utility to obtain said plurality of first digitized signals including the first reference digitized signal; and sampling said one or more second analog signals and said reference analog signal with said second sampling utility to obtain said one or more second digitized signals and said second digitized reference signal.

3. The method of claim 1 wherein sampling clocks of said first and second sampling utilities operate with sampling rates in a vicinity of a similar nominal sampling rate.

4. The method of claim 1 wherein each frame displaying by said ECG signals on the display presents a time interval of said ECG signals not exceeding a certain maximal duration, and wherein said reference analog signal is selected as one of said first analog signals being non-periodic and non-stationary within intervals of said certain maximal duration.

5. The method of claim 4 wherein said reference analog signal is a far-field ECG signal.

6. The method of claim 1 wherein said first and second medical devices comprise a plurality of ECG sensors that are adapted to sense said ECG signals in-situ during operation of the heart.

7. The method of claim 6 wherein one or more of the following:

at least one medical device of said first and second medical devices is a catheter adapted for insertion in to a body for at least one of probing and treating a heart; and at least one of said first and second sampling utilities is connected to a plurality of ECG sensors of said catheter that are adapted to measure said cardiac activity in-situ, during operation of the heart;

at least one medical device of said first and second medical devices is a surface ECG device comprising a plurality of ECG sensors adapted for placement on a body, externally thereto, for probing a heart; and at least one of said first and second sampling utilities is connected to said plurality of ECG sensors.

8. The method of claim 1 wherein said first medical device is a catheter adapted for being located within the heart during operation to sense intracardiac electrogram (IEGM) signals and said reference analog signal is an ECG signal obtained from at least one ECG sensor of said catheter.

9. The method of claim 8 wherein said catheter is adapted for insertion in to said heart and a plurality of ECG sensors of said catheter comprise multitude of ECG sensors arranged in said catheter for contacting a tissue of said heart during operation of the catheter, and at least one ECG sensor that is arranged in said catheter such that it is spaced from said tissue of the heart during said operation of the catheter, thereby enabling to sense a far-field ECG signal of the heart via said at least one ECG sensor and utilizing said far-field ECG signal as said reference analog signal.

10. The method of claim 1 comprise applying further processing to the synchronized first and second digitized signals to analyze or compute one or more properties associated with said electrocardiograms.

11. A method for synchronized streaming to a display of electrogram (ECG) signals obtained from a plurality of medical devices, the method comprising:

receiving, via a first data-link associated with a first utility of a first medical device, a first sequence of data-packets comprising a plurality of first digitized ECG signals regularly packaged and transmitted over said first data-link by the first utility;

receiving, via a second data-link associated with a second utility of a second medical device, a second sequence of data-packets comprising one or more second digitized ECG signals regularly packaged and transmitted over said second data-link by the second utility;

monitoring the receipt timings of data-packets regularly transmitted over each of said first and second data-links to determine statistics of communication latencies in each of said data-links;

determining standard deviations of the communication latencies of each said first and second data-links respectively;

setting a buffering duration by which to defer streaming of the ECG signals to the display in order to enable synchronized streaming of said first and second digitized ECG signals to the display, wherein the buffering duration is set to match a predetermined multiple of a largest standard deviation of said standard deviations of the communication latencies; and upon initialization of synchronized streaming of ECG signals to the display, deferring said synchronized streaming by said buffering duration;

buffering the first and second digitized ECG signals of the first and second sequences of data-packets received over said first and second data-links, in a buffer;

successively packaging successive sets of signal samples of said first and second digitized ECG signals retrieved from the buffer, according to their sampling order, to form a sequence of successive signal-frames to be streamed for display; and upon laps of said buffering duration, streaming said signal-frames to the display at a frame rate;

thereby mitigating said communication latencies and enabling pseudo real-time synchronized streaming to the display of ECG signals obtained via data-links associated with a plurality of medical devices.

12. The method of claim 11 wherein said packaging the successive sets of signal samples comprises down-sampling said signal samples of said first and second digitized ECG signals of said sets to from said signal frames with resolution suitable for presentation on said display.

13. The method of claim 11 wherein said consecutive sets of said successive sets of signal samples, which are used to from said signal-frames, include overlapping signal samples.

14. The method of claim 11 comprising determining standard deviations of the communication latencies of each said first and second data-links respectively and setting said buffering duration to match a predetermined multiple of a largest standard deviation of said standard deviations of the communication latencies.

15. The method of claim 11 wherein said buffering duration is set to a multiple of at least three times said largest standard-deviation of said latency, while not exceeding a predetermined maximal buffering duration permitted for said streaming.

16. A system to synchronized streaming to a display of electrocardiogram (ECG) signals obtained from a plurality of medical devices, the system comprises:

a synchronizer adapted to receive first and second pluralities of digitized signals respectively sampled by first and second sampling utilities from a corresponding first and second pluralities of analog signals respectively sensed by ECG sensors of at least one first medical device and at least one second medical device;

wherein the first plurality of digitized signals includes a first reference digitized signal that is sampled by the first sampling utility from an analog signal of said first plurality of analog signals that selected as a reference analog signal and is sensed by an ECG sensor of the first medical device, which is selected as reference ECG sensor; and wherein the second plurality of digitized signals includes a second reference digitized signal that is sampled by the second sampling utility from said reference analog signal and is sensed by the reference ECG sensor of the first medical device;

said synchronizer comprises:

a comparator adapted to compare between said first and second digitized reference signals; and a samples processor adapted for synchronizing between the plurality of first the digitized signals and the plurality of the second digitized signals by:

identifying, based on said results of the comparison, an extra sample obtained in each digitized signal of one of the first or second plurality of digitized signals obtained from one of the first or second sampling utility respectively; and wherein said extra sample results from a difference between sampling rates of the first and second sampling utilities; and removing said extra sample from each said digitized signal of the first or second digitized signals; thereby obtaining synchronized signals of said first and second pluralities of digitized signals; and said synchronizer being associated with a streamer that is adapted to concurrently stream the synchronized signals of said first and second pluralities of digitized signals for display on said display.

17. The system of claim 16 wherein said first and second pluralities of digitized signals are ECG signals; and wherein each frame displaying said ECG signals on the display, presents a time interval of said ECG signals not exceeding a certain maximal duration; and said reference analog signal is selected as one of said first analog signals being non-periodic and non-stationary within intervals of said certain maximal duration.

18. The system of claim 17 wherein said at least one first medical device includes a catheter that is adapted for being located within a heart during operation thereof to sense intracardial electrogram (IEGM) signals; and wherein said reference ECG sensor is an ECG sensor arranged in said catheter such that it is spaced from a tissue of the heart during said operation and adapted to obtain said reference analog signal as a far-field ECG signal.

19. The system of claim 16 wherein one or more of the following:

the system further comprises at least one of the following:

said at least one first medical device; said at least one second medical device; said first sampling utility; said second sampling utility; and said display;

said at least one first and at least one second medical devices comprise a plurality of ECG sensors that are adapted to sense ECG signals in-situ during operation of a heart;

at least one medical device of said first and second medical devices is a catheter adapted for insertion into a body for at least one of probing and treating a heart; and at least one of said first and second sampling utilities is connected to a plurality of ECG sensors of said catheter;

at least one medical device of said first and second medical devices is a surface ECG device comprising a plurality of ECG sensors adapted for placement on a body, externally thereto, for probing a heart; and at least one of said first and second sampling utilities is connected to said plurality of ECG sensors.

20. A system for synchronized streaming to a display of electrocardiogram (ECG) signals obtained from a plurality of medical devices, the system comprises:

a data communication utility configured and operable to receive, via first and second communication links associated respectively with first and second utilities, respective first and second sequences of data-packets; whereby the first sequence of data-packets comprises a plurality of first digitized ECG signals, which are sampled from ECG sensors of at least one first medical device and regularly packaged and transmitted over said first communication link by the first utility; and the second sequence of data-packets comprises a plurality of second digitized ECG signals, which are sampled from ECG sensors of at least one second medical device and regularly packaged and transmitted over said second communication link by the second utility;

a packet synchronizer comprising:

a communication-links monitor that is connected to said data communication utility and adapted to monitor receipt timings of data-packets transmitted over each of said first and second communication links and thereby determine statistics of communication latencies of each of the first and second communication links, wherein said communication-links monitor is adapted to process said receipt timings of the data-packets and thereby determine standard deviations of the communication latencies of each said first and second communication links respectively; and a buffering utility comprising a buffer and configured and operable to utilize said statistics of the communication latencies to determine a buffering duration by which to buffer the first and second digitized ECG signals of said data-packets and defer streaming of the ECG signals to the display, in order to enable synchronized streaming of said first and second digitized ECG signals to the display; and wherein upon initialization of synchronized streaming of ECG signals to the display, said buffering utility is adapted to defer said synchronized streaming by said buffering duration, and buffer the first and second digitized ECG signals of the first and second sequences of data-packets received over said first and second communication links in said buffer, wherein said buffering utility is adapted to set said buffering duration to match a predetermined multiple of a largest standard deviation of said standard deviations of the communication latencies;

a frame-packager configured and operable for successively retrieving and packaging successive sets of signal samples of said first and second digitized ECG signals stored in the buffer, according to their sampling order, to form a sequence of successive signal-frames to be streamed for display; and a streamer adapted to operate upon laps of said buffering duration for streaming said signal- frames to the display at a frame rate.

21. The system of claim 20 wherein said frame-packager comprises the synchronizer of claim 16 and is configured and operable for synchronizing between the signal samples of the first and second pluralities digitized signals and identify and remove extra samples obtained in each digitized signal of the first or second digitized signals as a result of a difference between sampling rates of the first and second utilities.

22. The system of claim 20 wherein said frame-packager comprises a re-sampler adapted to down-sample said first and second digitized ECG signals to from said signal frames with resolution suitable for presentation on said display.

\* \* \* \* \*